(12) United States Patent
Kalnes et al.

(10) Patent No.: US 7,663,012 B2
(45) Date of Patent: *Feb. 16, 2010

(54) CONVERSION OF DIMETHYLETHER TO PROPYLENE USING MOVING BED TECHNOLOGY

(75) Inventors: Tom N. Kalnes, LaGrange, IL (US); Daniel H. Wei, Naperville, IL (US); Bryan K. Glover, Algonquin, IL (US)

(73) Assignee: UOP LLC, Des Plaines, IL (US)

( * ) Notice: Subject to any disclaimer, the term of this patent is extended or adjusted under 35 U.S.C. 154(b) by 72 days.

This patent is subject to a terminal disclaimer.

(21) Appl. No.: 12/115,788

(22) Filed: May 6, 2008

(65) Prior Publication Data

US 2008/0242910 A1 Oct. 2, 2008

Related U.S. Application Data

(63) Continuation-in-part of application No. 10/876,394, filed on Jun. 25, 2004, now Pat. No. 7,371,915.

(51) Int. Cl.
*C07C 1/00* (2006.01)
(52) U.S. Cl. ...................... 585/640; 585/638
(58) Field of Classification Search ............. 585/639, 585/640
See application file for complete search history.

(56) References Cited

U.S. PATENT DOCUMENTS

| | | | |
|---|---|---|---|
| 4,061,724 A | 12/1977 | Grose et al. | 423/335 |
| 4,073,865 A | 2/1978 | Flanigen et al. | 423/339 |
| 4,310,440 A | 1/1982 | Wilson et al. | 252/435 |
| 4,387,263 A | 6/1983 | Vogt et al. | 585/640 |

(Continued)

FOREIGN PATENT DOCUMENTS

EP 0448000 B1 5/1994

(Continued)

OTHER PUBLICATIONS

Rothaemal et al., "Demonstrating the New Methanol to Propylene (MTP) Process", Mar. 2003, ERTC Petrochemical Conference, Paris, France.

(Continued)

*Primary Examiner*—In Suk Bullock
(74) *Attorney, Agent, or Firm*—Mark Goldberg

(57) ABSTRACT

The average cycle propylene selectivity of an oxygenate to propylene (OTP) process using one or more fixed beds of a dual-function oxygenate conversion catalyst is substantially enhanced by the use of moving bed reactor technology in the hydrocarbon synthesis portion of the OTP flow scheme in lieu of fixed bed technology coupled with the selection of a catalyst on-stream cycle time of 200 hours or less. Those provisions hold the build-up of coke deposits on the catalyst to a level which does not substantially degrade dual-function catalyst activity, oxygenate conversion and propylene selectivity, thereby enabling maintenance of propylene average cycle yield at essentially start-of-cycle levels. The propylene average cycle yield improvement enabled by the present invention over that achieved by the fixed bed system of the prior art using the same or a similar catalyst system is of the order of about 1.5 to 5.5 wt-% or more.

14 Claims, 1 Drawing Sheet

U.S. PATENT DOCUMENTS

| | | | |
|---|---|---|---|
| 4,433,188 A | 2/1984 | Hoelderich et al. | 585/640 |
| 4,440,871 A | 4/1984 | Lok et al. | 502/214 |
| 4,527,001 A | 7/1985 | Kaiser | 585/643 |
| 4,554,143 A | 11/1985 | Messina et al. | 423/306 |
| 4,579,999 A | 4/1986 | Gould et al. | 585/312 |
| 4,587,373 A | 5/1986 | Hsia | 585/639 |
| 4,677,243 A | 6/1987 | Kaiser | 585/638 |
| 4,752,651 A | 6/1988 | Kaiser | 585/640 |
| 4,793,984 A | 12/1988 | Lok et al. | 423/306 |
| 4,853,197 A | 8/1989 | Wilson et al. | 423/306 |
| 4,873,390 A | 10/1989 | Lewis et al. | 585/638 |
| 5,095,163 A | 3/1992 | Barger | 585/640 |
| 5,126,308 A | 6/1992 | Barger et al. | 502/214 |
| 5,157,181 A | 10/1992 | Stine et al. | 585/329 |
| 5,191,141 A | 3/1993 | Barger et al. | 585/640 |
| 6,121,504 A | 9/2000 | Kuechler et al. | 585/640 |
| 6,455,749 B1 | 9/2002 | Vaughn | 585/640 |
| 7,015,369 B2 | 3/2006 | Hack et al. | 585/640 |
| 7,371,915 B1 * | 5/2008 | Kalnes et al. | 585/640 |

FOREIGN PATENT DOCUMENTS

GB 2171718 A 9/1986

OTHER PUBLICATIONS

Paper "Insights into Gas to Propylene, GTP®/MTP® Technology" by Dr. Waldemar Liebner, Lurgi AG, Frankfurt am Main; Germany, presented at Propylene Trade & Derivatives Markets, Singapore, Oct. 24-25, 2005.

* cited by examiner

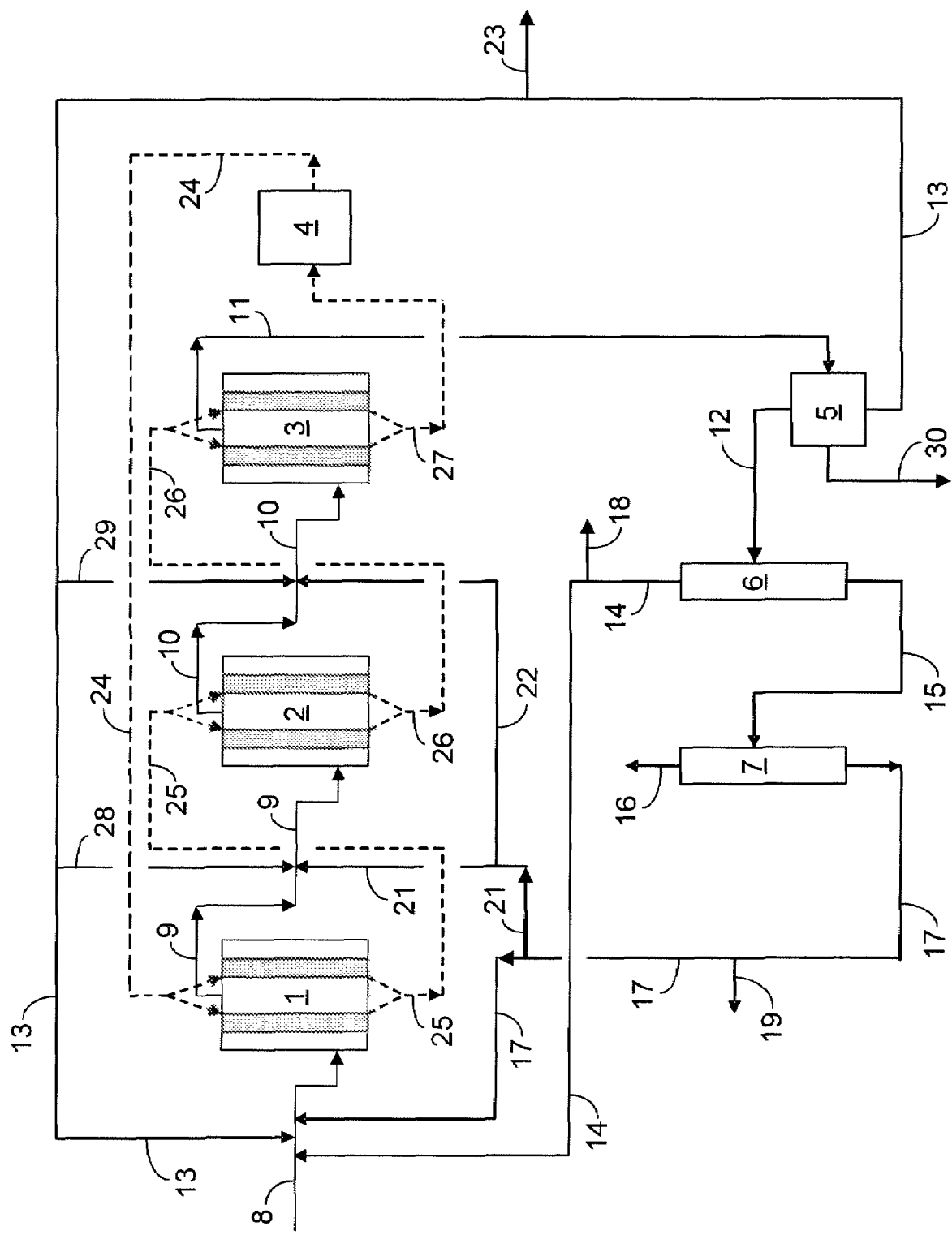

US 7,663,012 B2

CONVERSION OF DIMETHYLETHER TO PROPYLENE USING MOVING BED TECHNOLOGY

CROSS-REFERENCE TO RELATED APPLICATION

This application is a Continuation-In-Part of application Ser. No. 10/876,394 filed Jun. 25, 2004, now U.S. Pat. No. 7,371,915, the contents of which are hereby incorporated by reference in its entirety.

FIELD OF THE INVENTION

The present invention relates generally to the use of moving bed technology in the hydrocarbon synthesis reaction zone of a oxygenate to propylene (OTP) process coupled with a catalyst on-stream cycle time selected to result in a level of catalyst coking that does not significantly degrade the activity and selectivity of the dual-function catalyst used in this OTP process. The oxygenate feed is mostly, if not essentially all, dimethylether (DME). These two provisions in turn lead to a sharp improvement in the average propylene yield achievable by the modified process over the on-stream catalyst cycle of this OTP process relative to the average cycle propylene yield that is achievable by a prior art process that uses fixed bed technology for the oxygenate to hydrocarbon conversion reaction and operates with longer catalyst cycle times. The present invention more specifically relates to an improved catalytic oxygenate to propylene process that uses a combination of moving bed technology and a catalyst on-stream cycle time of 200 hours or less to hold average cycle catalytic activity and selectivity at essentially the start of cycle levels during the entire on-stream cycle, thereby sharply improving the average propylene yield achieved by the catalyst over its life cycle relative to that achievable with the same catalyst in a fixed bed system. The key to the present invention involves recognition that propylene selectivity achievable over dual-function OTP catalysts systems known in the art is very sensitive to deactivation by coke deposition and by hydrothermal deactivation (caused by exposure to high temperatures in the presence of steam)—particularly where common countermeasures are taken such as reactor temperature increase in order to maintain catalyst activity. Stated another way, the key to the present invention is the fact that propylene selectivity in an OTP catalytic process can be continuously maintained at essential start-of-run levels if moving bed technology is used to minimize and control detrimental coke deposition to the point where start-of-run catalyst activity and selectivity for the dual-function OTP catalyst system is not compromised.

BACKGROUND OF THE INVENTION

A major portion of the worldwide petrochemical industry is concerned with the production of light olefin materials and their subsequent use in the production of numerous important chemical products via polymerization, oligomerization, alkylation and the like well-known chemical reactions. Light olefins include ethylene, propylene and mixtures thereof. These light olefins are essential building blocks for the modern petrochemical and chemical industries. The major source for these materials in present day refining is the steam cracking of petroleum feeds. For various reasons including geographical, economic, political and diminished supply considerations, the art has long sought a source other than petroleum for the massive quantities of raw materials that are needed to supply the demand for these light olefin materials. In other words, the holy grail of the R & D personnel assigned to work in this area is to find a way to effectively and selectively use alternative feedstocks for this light olefin production application, thereby lessening dependence of the petrochemical industry on petroleum feedstocks. A great deal of the prior art's attention has been focused on the possibility of using hydrocarbon oxygenates and more specifically methanol or dimethylether (DME) as a prime source of the necessary alternative feedstock. Oxygenates are particularly attractive because they can be produced from such widely available materials as coal, natural gas, recycled plastics, various carbon waste streams from industry and various products and by-products from the agricultural industry. The art of making methanol and other oxygenates from these types of raw materials is well established and typically involves the use of one or more of the following procedures: (1) manufacture of synthesis gas by any of the known techniques typically using a nickel or cobalt catalyst followed by the well-known methanol synthesis step using relatively high pressure with a copper-based catalyst; (2) selective fermentation of various organic agricultural products and by-products in order to produce oxygenates; or (3) various combinations of these techniques.

Given the established and well-known technologies for producing oxygenates from alternative non-petroleum raw materials, the art has focused on different procedures for catalytically converting oxygenates such as methanol into the desired light olefin products in order to make an oxygenate to olefin (OTO) process. These light olefin products that are produced from non-petroleum based raw materials must of course be available in quantities and purities such that they are interchangeable in downstream processing with the materials that are presently produced using petroleum sources. Although many oxygenates have been discussed in the prior art, the principal focus of the two major routes to produce these desired light olefins has been on methanol conversion technology primarily because of the availability of commercially proven methanol synthesis technology. A review of the prior art has revealed essentially two major techniques that are discussed for conversion of methanol to light olefins (MTO). The first of these MTO processes is based on early German and American work with a catalytic conversion zone containing a zeolitic type of catalyst system. Representative of the early German work is U.S. Pat. No. 4,387,263 which was filed in May of 1982 in the U.S. without a claim for German priority. This '263 patent reports on a series of experiments with methanol conversion techniques using a ZSM-5 type of catalyst system wherein the problem of DME by-product recycle is a major focus of the technology disclosed. Although good yields of ethylene and propylene were reported in this '263 patent, they unfortunately were accompanied by substantial formation of higher aliphatic and aromatic hydrocarbons which the patentees speculated might be useful as an engine fuel and specifically as a gasoline-type of material. In order to limit the amount of this heavier material that is produced, the patentees of the '263 patent propose to limit conversion to less than 80% of the methanol charged to the MTO conversion step. This operation at lower conversion levels necessitated a critical assessment of means for recovering and recycling not only unreacted methanol but also substantial amounts of a DME intermediate product. The focus then of the '263 patent invention was therefore on a DME and methanol scrubbing step utilizing a water solvent in order to efficiently and effectively recapture the light olefin value of the unreacted methanol and of the intermediate reactant DME.

This early MTO work with a zeolitic catalyst system was then followed up by the Mobil Oil Company who also investigated the use of a zeolitic catalyst system like ZSM-5 for purposes of making light olefins. U.S. Pat. No. 4,587,373 is representative of Mobil's early work and it acknowledged and distinguished the German contribution to this zeolitic catalyst based MTO route to light olefins. The inventor of the '373 patent made two significant contributions to this zeolitic MTO route the first of which involved recognition that a commercial plant would have to operate at pressure substantially above the preferred range that the German workers in this field had suggested in order to make the commercial equipment of reasonable size when commercial mass flow rates are desired. The '373 patent recognized that as you move to higher pressure for the zeolitic MTO route in order to control the size of the equipment needed for commercial plant there is a substantial additional loss of DME that was not considered in the German work. This additional loss is caused by dissolution of substantial quantities of DME in the heavy hydrocarbon oil by-product recovered from the liquid hydrocarbon stream withdrawn from the primary separator. The other significant contribution of the '373 patent is manifest from inspection of the flow scheme presented in FIG. 2 which prominently features a portion of the methanol feed being diverted to the DME absorption zone in order to take advantage of the fact that there exist a high affinity between methanol and DME thereby downsizing the size of the scrubbing zone required relative to the scrubbing zone utilizing plain water that was suggested by the earlier German work.

Primarily because of an inability of this zeolitic MTO route to control the amounts of undesired $C_4^+$ hydrocarbon products produced by the ZSM-5 type of catalyst system, the art soon developed a second MTO conversion technology based on the use of a non-zeolitic molecular sieve catalytic material. This branch of the MTO art is perhaps best illustrated by reference to UOP's extensive work in this area as reported in numerous patents of which U.S. Pat. No. 5,095,163; U.S. Pat. No. 5,126,308 and U.S. Pat. No. 5,191,141 are representative. This second approach to MTO conversion technology was primarily based on using a catalyst system comprising a non-zeolitic molecular sieve, generally a metal aluminophosphate (ELAPO) and more specifically a silicoaluminophosphate molecular sieve (SAPO), with a strong preference for a SAPO species that is known as SAPO-34. This SAPO-34 material was found to have a very high selectivity for light olefins with a methanol feedstock and consequently very low selectivity for the undesired corresponding light paraffins and the heavier materials. This ELAPO catalyzed MTO approach is known to have at least the following advantages relative to the zeolitic catalyst route to light olefins: (1) greater yields of light olefins at equal quantities of methanol converted; (2) capability of direct recovery of polymer grade ethylene and propylene without the necessity of the use of extraordinary physical separation steps to separate ethylene and propylene from their corresponding paraffin analogs; (3) sharply limited production of by-products such as stabilized gasoline; (4) flexibility to adjust the product ethylene-to-propylene weight ratios over the range of 1.5:1 to 0.75:1 by minimal adjustment of the MTO conversion conditions; and (5) significantly less coke make in the MTO conversion zone relative to that experienced with the zeolitic catalyst system.

The classical OTO technology produces a mixture of light olefins primarily ethylene and propylene along with various higher boiling olefins. Although the classical OTO process technology possesses the capability of shifting the major olefin product recovered therefrom from ethylene to propylene by various adjustments of conditions maintained in the reaction zone, the art has long sought an oxygenate to propylene (OTP) technology that would provide better yields of propylene relative to the classical OTO technology. The driving force for this shift in emphasis towards propylene is the growth rate of the propylene market versus the growth rate of the ethylene market. The existing sources of propylene production in the marketplace are primarily based on conventional steam cracking of naphtha, LPG streams, propane streams and the like. Another major existing source of propylene is of course the olefins that are produced in a fluid catalytic cracking (FCC) hydrocarbon conversion process in the modern day refinery. Because the basic raw material used in an OTO process is derived from natural gas which is widely available particularly in remote areas of the world but unfortunately markets for this gas are typically not conveniently available near the location of the remote gas fields. These remote gas fields tend to be quite large and because of the relatively well-developed technology for converting natural gas to methanol and other oxygenates are viewed by those skilled in this art and being the next logical source of large-scale propylene production provided a commercially acceptable OTP process can be established which possesses intrinsic high selectivity for the desired propylene product.

Workers at Lurgi Oel Gas Chemie GmbH have recently announced a new fixed bed methanol to propylene (MTP) process which according to Lurgi offers the potential to satisfy the arts' thirst for a propylene selective OTO type of process. It appears that the basic flow scheme and technical details of the Lurgi process offering in this field have been relatively recently disclosed in U.S. Pat. No. 7,015,369 and describes a process for selectively producing propylene from a feedstock which comprises methanol and/or DME. Analysis of the two figures attached to this patent publication make it clear that Lurgi contemplates a reactor flow configuration for the oxygenate to propylene (OTP) synthesis portion of its flow scheme wherein three reactors are utilized with fixed beds of oxygenate conversion catalysts in a parallel flow arrangement with respect to the oxygenate feed. The reactors are connected in a serial flow arrangement with respect to the effluents of the first reactor and the second reactor. The dual function OTP catalyst system taught as being useful in this flow scheme is rather narrowly defined in paragraph [0005] of this patent publication as a pentasil-type (i.e. ZSM-5 type) having an alkali content less than 380 ppm and a zinc oxide content of less than 0.1 wt-% coupled with a restriction on cadmium oxide content of the same amount. The teachings with respect to this catalyst are derived from a European patent, EP-B-0448000, filed by Sud Chemie and Lurgi claiming priority from an original German application that was filed in March of 1990. Thus the catalyst contemplated for use in Lurgi's flow scheme is well known to those skilled in this art. According to Lurgi's marketing presentation, the on-stream portion of the process cycle for this MTP process is expected to be 500 to 700 hours before in situ regeneration becomes necessary. (See Rothaemel et al. "Demonstrating the New Methanol to Propylene (MTP) Process" presented to the ERTC Petrochemical Conference in March of 2003 at Paris, France). The activity-stability of the MTP catalyst in this Lurgi presentation show a significant drop in conversion activity over the first five cycles with each cycle being terminated after the oxygenate conversion level drops to about 94% to 95% of the oxygenate feed. No mention is made in this paper of a corresponding drop in propylene selectivity and instead the average propylene selectivity over the on-stream cycle is discussed and a table presented showing that it ranges from 30% to 40% of the converted products with a number between 68% to 71% presented as an estimate of the average cycle selectivity for propylene over the 500 to 700 hour cycle length expected to be achieved by this flow scheme. Lurgi also contemplates that at the end of the cycle when the conversion has dropped to a level of about 94% of the carbon equivalent in the feed that the reactors will be shut down and the catalyst regenerated using a air/nitrogen mixture to burn off the detrimental coke deposits.

Although Lurgi does not state exactly what countermeasures it takes during its process cycle in order to compensate for the falloff in activity of its dual-function MTP catalyst due to coke deposition, we believe that Lurgi undoubtedly follows the conventional procedure for compensating for activity decay in a catalytic operation involving an increase in the average reactor temperature in order to attempt to hold conversion in the targeted range of greater than 94% of the oxygenate charge. Under these circumstances it is our considered opinion based on experimental results with similar dual-function catalysts and similar feeds that the falloff of propylene selectivity over the cycle is accelerated by the coke deposition and by the attempt to take countermeasures to compensate and we believe that the selectivity falloff will be greater than the activity falloff by a factor of 1.25 to 3.5 or more depending somewhat on the exact composition of the catalyst used and the operating condition changes that are made during the cycle to attempt to compensate for the falloff in activity.

The problem addressed by the present invention is then to modify this MTP process of the prior art in order to enhance its average propylene selectivity over the on-stream cycle and thereby diminish the requirement for recycle of olefin products other than propylene in order to compensate for lower propylene selectivity. We have now discerned that propylene selectivity is a function not only of reaction conditions but also of average coke level deposited on the OTP conversion catalyst during the on-stream portion of the process cycle. Put another way we have now found that average propylene selectivity in an OTP process can be significantly enhanced if the amount of detrimental carbonaceous deposits laid down on the catalyst during the on-stream portion of the process cycle is held to a level such that the OTP catalyst activity is not significantly diminished and oxygenate conversion is maintained over the process cycle at essentially start of cycle level. By the use of the term "not significantly diminished" we intend to mean that the conversion level at constant conditions is not allowed to fall more than 2 to 3% during the course of the on-stream catalyst cycle. Quite surprisingly we have also discerned that if this restriction is put on such an OTP process then the average propylene selectivity over the cycle will be improved by about 1.5% to 5.5% or more depending somewhat on the countermeasures taken in the prior art process as the catalyst performance degrades due to the high level of coke deposition on the catalyst during the latter portion of the on-stream cycle. In other words if the propylene selectivity of the prior art OTP process is in the range of 30% to 40% of the carbon-containing MTP products from the OTP reactions we would anticipate the use of our invention to enable an improvement in this number to a level of 31.5% to 45.5% or more, thereby significantly improving the economics of the process. In sharp contrast to the OTP process of the prior art, our invention envisions replacing the fixed bed technology in the olefin synthesis reactors of the prior art with moving bed technology operating with a catalyst circulation rate through the reactors such that the catalyst on-stream cycle time is 200 hours or less. Under these conditions the initial on-stream oxygenate conversion of the OTP process does not drop by more than 2 to 3% thereby enabling maintenance of propylene selectivity at essentially start of run condition.

SUMMARY OF THE INVENTION

The primary objective of the present invention is to provide a realistic and technically feasible solution to the problem of propylene selectivity loss during the on-stream cycle of the prior art fixed bed OTP process. A secondary objective is to improve the economics of the prior art OTP process in order to diminish the amount of olefins other than propylene that must be recycled in order to maintain propylene selectivity at the target level. Another object of the present invention is to avoid severe deactivation of the dual-function OTP catalyst utilized in the OTP process in order to minimize the severity of the regeneration step that is needed in order to restore fresh catalyst activity, thereby minimizing hydrothermal damage and prolonging catalyst life. A more general objective is to shift the emphasis in the art for OTP conversion away from a fixed bed system towards a moving bed technology that minimizes attrition losses associated with handling of the sensitive dual-function OTP catalyst particles.

In one embodiment the instant invention is a continuous process for the selective conversion of an oxygenate feed to a propylene utilizing moving bed technology and a catalyst circulation rate selected to maintain catalyst performance at essentially start of cycle levels, thereby enhancing the average cycle yield of propylene and minimizing oxygenate breakthrough into the product stream. In the first step of the process an oxygenate feed and a diluent in an amount corresponding to about 0.1:1 to 5:1 moles of diluent per mole of oxygenate is contacted with a dual-function catalyst containing a molecular sieve known to have the ability to convert at least a portion of the oxygenate to propylene and to interconvert $C_2$ and $C_4^+$ olefins to $C_3$ olefins. This OTP contacting step is performed in a reaction zone containing at least one moving bed reactor which is operated at oxygenate conversion conditions selected to convert oxygenate to propylene and at a catalyst circulation rate through the reaction zone selected to result in a catalyst on-stream cycle time of 200 hours or less. An effluent stream is then withdrawn from the reaction zone and found to contain major amounts of a $C_3$ olefin product and a water by-product and lesser amounts of a $C_2$ olefin, $C_4^+$ olefins, $C_1$ to $C_4^+$ saturated hydrocarbons and minor amounts of unreacted oxygenate, by-product oxygenates and aromatic hydrocarbons. In the second step this effluent stream is passed to a separation zone and therein cooled and separated into a vaporous fraction rich in $C_3$ olefins, a water fraction containing unreacted oxygenate and by-product oxygenates and a liquid hydrocarbon fraction containing heavier olefins, heavier saturated hydrocarbons and minor amounts of aromatic hydrocarbons. At least a portion of the water fraction recovered in this separation step is then recycled to the oxygenate conversion step to provide at least a portion of the diluent used therein. The vaporous fraction recovered in this separation step is further separated in a second separating zone into a $C_2$ olefin first fraction, a $C_3$ olefin-rich product fraction and a first $C_4^+$ olefin-rich fraction. The $C_3$ olefin-rich product fraction is then recovered as a principal product stream from the present process and at least a portion of the $C_2$ olefin-rich fraction or of the first $C_4^+$ olefin-rich fraction or of a mixture of these fractions is recycled to the first step in order to interconvert these materials into additional quantities of the desired propylene product. In the last step of the process in this embodiment a stream of coke-containing dual-function catalyst particles is withdrawn from the reaction zone, oxidatively regenerated with an oxygen-containing stream in a regeneration zone and a stream of regenerated catalyst particles is returned to the reaction zone in order to provide regenerated catalyst for circulation therethrough.

A second embodiment involves a continuous process for the selective conversion of an oxygenate feed to propylene as described in the first embodiment wherein the dual-function catalyst contains a zeolitic molecular sieve having a structure corresponding to ZSM-5, or an ELAPO molecular sieve having a structure corresponding to SAPO-34 or a mixture of these materials.

Another embodiment comprises a continuous process for selective conversion of an oxygenate feed to propylene as described above in the first embodiment wherein the reaction zone contains at least 3 moving bed reactors which are connected in a serial flow or parallel flow configuration with respect to oxygenate feed and in a serial flow configuration with respect to the stream of catalyst particles that passes therethrough.

A highly preferred embodiment of the present invention comprises a continuous process for the selective conversion of an oxygenate feed to propylene as described above in the first embodiment wherein the oxygenate feed contains methanol or dimethylether or a mixture thereof. In this embodiment the instant process is referred to herein as a methanol to propylene embodiment (MTP).

A very highly preferred embodiment of the present invention comprises a continuous process for the selective conversion of an oxygenate feed to propylene as described above in the first embodiment wherein the oxygenate feed consists of at least 75% by weight, preferably at least 90% by weight, more preferably 95%, even more preferably 99% and most preferably essentially all dimethylether.

A high propylene yield embodiment of the instant process involves the continuous process for selective conversion of an oxygenate feed to propylene as described in any of the previous embodiments wherein the liquid hydrocarbon fraction recovered in the first separation step is further separated into a second $C_4^+$ olefin-rich fraction and a naphtha product fraction and at least a portion of the $C_4^+$ olefin-rich fraction is recycled to the OTP conversion step in order to interconvert these heavier olefins into propylene.

Other objects, embodiments, advantages and features of the present invention will be clear to somebody of ordinary skill in the chemical engineering art from a detailed examination of the following description of the invention as well as the information contained in the attached drawing.

BRIEF DESCRIPTION OF THE DRAWING

The FIGURE is a process flow diagram of a preferred embodiment of the present invention which portrays the essential interconnections and interrelationships between the various operating zones preferably utilized to selectively and continuously convert an oxygenate feed to propylene wherein three moving bed reaction zones are utilized in a preferred serial flow configuration with respect to oxygenate feed and with respect to catalyst circulation. In this drawing, lines utilized for circulation of reactants and products are drawn as solid lines whereas lines exclusively used for circulation of catalyst particles are drawn as dotted lines.

TERMS AND CONDITIONS DEFINITIONS

The following terms and conditions are used in the present specification with the following meanings: (1) A "portion" of a stream means either an aliquot part that has the same composition as the whole stream or a part that is obtained by eliminating a readily separable component therefrom (e.g. if the stream contains hydrocarbons in admixture with steam, then after condensation of a major portion of the steam, it comprises an aqueous portion and a hydrocarbon portion). (2) An "overhead" stream means the net overhead recovered from the specified zone after recycle of any portion to the zone for reflux or any other reason. (3) A "bottom" stream means the net bottom stream from the specified zone obtained after recycle of any portion for purposes of reheating and/or reboiling and/or after any phase separation. (4) A line or reactor is "blocked-off" when it contains one or more valves that are set to a position that prevents flow through the line or reactor. (5) Presence of necessary compressors and/or pumps is understood when flow is shown from a zone of relatively low pressure to a zone of higher pressure. (6) Presence of necessary heating and/or cooling means is implied when flow is shown between zones operating at different temperatures. (7) An ingredient is "lifted" or "stripped" when it is concentrated in the overhead stream withdrawn from the specified zone. (8) A "vapor" stream means a stream containing one or more components in the gaseous state. (9) The term "light olefins" means ethylene, propylene and mixtures thereof. (10) The expression "OTP" process means a process for converting an oxygenate to propylene and in a preferred embodiment when the oxygenate is methanol the OTP process is referred to as an MTP process herein. In a highly preferred embodiment, the oxygenate consists essentially of dimethylether (DME). (11) The term "oxygenate" means an oxygen-substituted aliphatic hydrocarbon preferably containing 1 to 4 carbon atoms. (12) The term "catalyst on-stream cycle time" means the length of time the catalyst particle is exposed to feed at conversion conditions before being withdrawn from the reaction zone for regeneration (moving bed system) or the reaction is blocked off for regeneration (fixed bed system). (13) The term "propylene average cycle yield" means the total propylene yield during the catalyst on-stream cycle time divided by the catalyst on-stream cycle time and by the total amount of oxygenate feed converted during the catalyst on-stream cycle time. (14) The term "dual-functional" means that the OTP catalyst catalyzes both the OTP reactions and the olefin interconversion reactions necessary to convert $C_2$ and $C_4^+$ olefin to propylene.

DETAILED DESCRIPTION OF THE INVENTION

In the instant OTP process the feedstream comprises one or more oxygenates. The term "oxygenate" is employed herein to include alcohols, ethers, and carbonyl compounds (e.g. aldehydes, ketones, carboxylic acids, and the like). The oxygenate feedstock preferably contains at least one oxygen atom and about 1 to 10 carbon atoms and, and preferably, contains from about 1 to 4 carbon atoms. Suitable oxygenates include lower straight or branched chain alkanols, and their unsaturated counterparts. Representatives of suitable oxygenate compounds include methanol, dimethyl ether (DME), ethanol, diethyl ether, methylether, formaldehyde, dimethyl ketone, acetic acid, and mixtures thereof.

In the OTP conversion step of the present invention, the oxygenate feedstock is catalytically converted to hydrocarbons containing aliphatic moieties such as—but not limited to—methane, ethane, ethylene, propane, propylene, butylene, and limited amounts of other higher aliphatics by contacting the feedstock with a dual-function OTP catalyst. A diluent is not absolutely required but is a useful option to maintain the selectivity of the catalyst to produce light olefins, particularly propylene. The use of a diluent such as steam can provide certain equipment cost and thermal efficiency advantages as well as lowering the partial pressure of the oxygenate reactants, thereby increasing selectivity to olefins. The phase change between steam and liquid water can also be employed to advantage in transferring heat between the feedstock and the reactor effluent, and the separation of the steam diluent from the product requires simple condensation of the water to separate the water from the hydrocarbon products.

A diluent is used in the present invention in order to control partial pressure of the oxygenate reactant in the OTP conversion zone in order to shift the selectivity towards propylene. Suitable diluents for use in the present invention include helium, argon, nitrogen, carbon monoxide, carbon dioxide, hydrogen, water, $C_1$ through $C_5$ paraffins, aromatic hydrocarbons and mixtures of these materials. Preferred diluents are water, methane, an aromatic compound, and mixtures thereof. The best diluents are relatively inert at the conditions maintained in the OTP reaction zone. An especially preferred diluent for use in the present invention is water since it is relatively easily recovered from the product effluent stream utilizing condensation techniques. The amount of diluent used will be selected from the range from about 0.1:1 to 5:1 moles of diluent per mole of oxygenate and preferably 0.5:1 to 2:1 in order to lower the partial pressure of the oxygenates to a level which favors production of propylene. Some of the embodiments of the present invention envision recycling of certain olefinic streams that contain significant amounts of olefins other than propylene and saturated hydrocarbons. These recycle streams will thus furnish diluent to the OTP reaction zone and therefore the amount of diluent that must be added to the OTP reaction zone in order to achieve the target diluent to oxygenate mole ratio will diminish once the OTP reaction zone is started up in embodiments using one or more of these hydrocarbon recycle streams. In the most preferred case where water is used as the diluent the amount of water charged to the OTP reaction zone during startup will diminish in proportion to the amount of saturated hydrocarbons and other inert materials that are recycled to this reaction zone.

The conversion conditions used in the OTP reaction zone in accordance with the present invention are carefully chosen to favor the production of propylene from the oxygenate charged in the feed. The art has already established an oxygenate conversion temperature range of about 350° to 600° C. as being effective for the conversion of oxygenate over the known oxygenate conversion catalyst. The lower portion of this oxygenate conversion temperature range is known to favor the production of propylene with the upper portion favoring the production of ethylene at the expense of propylene. Preferred inlet temperatures to the OTP reaction zone are therefore in the range of 350° to 500° C. and more preferably in the range of about 400° to 500° C. The temperature increase across each of the OTP reactors is preferably held to a number which is in the range of 20° to 80° C. in order to avoid the acceleration of coke deposition on the catalyst that is experienced when the temperature of the tail end of the individual reactors is allowed to build to levels beyond those contemplated by the present invention. There are numerous methods known to those of ordinary skill in this art for controlling the temperature increase in a reaction zone and most of them involved utilization of multiple beds of catalyst in separate reactors with inner bed cooling utilizing appropriate heat exchange means and/or addition of relatively cool amounts of recycle streams, or portions of the oxygenate feed and/or the diluents that is utilized in the zone. In the particular case contemplated by the present invention the use of lighter and heavier olefin interconversion reactions which are known to be mildly endothermic will also help to control reactor temperature increase to the specified range. As will be shown by reference to the attached drawing, the preferred mode of operation of the present invention is to use at least 3 moving bed reactors with interbed quench achieved at least in part by the use of relatively cool recycle streams to provide additional quantities of reactants and diluent.

The oxygenate to propylene conversion step is effectively carried out over a wide range of pressures including inlet total pressures between about 0.1 atm (10.1 kPa) up to about 100 atm (10.1 mPa) but it is well known that the formation of lighter olefins like propylene are favored at low pressure conditions. It is thus preferred to use an inlet pressure of about 1 to 3 atm (101.3 to 304 kPa) and best results are achieved at about 136 to 343 kPa (5 to 35 psig).

The contact time of the reactants with the dual-function catalyst is ordinarily measured in relative terms of a Weight Hourly Space Velocity (WHSV) which is calculated on the basis of a mass hourly flow rate of the sum of the mass of oxygenate reactants passed to the OTP conversion zone plus the mass of any reactive hydrocarbon material present in the feedstream or any of the recycle streams divided by the mass of the dual-function catalyst present in the OTP conversion zone. Those skilled in the art will recognize that the contact time of the reactants with the catalyst is proportional to the inverse of the WHSV such that as the WHSV increases contact time decreases and conversely a decrease in WHSV produces an increase in contact time. WHSV for use in the OTP conversion zone associated with the present invention can range from about 0.1 to 100 $hr^{-1}$, with a preferred range being about 0.5 to 20 $hr^{-1}$, with best results ordinarily attained in the range of 0.5 to 10 $hr^{-1}$.

In the oxygenate to propylene conversion process of interest to the present invention it is preferred to use a dual-function catalyst having the capability of converting oxygenates to propylene as well as the capability of interconverting olefins other than propylene to propylene. Any of the catalytic materials known to the art that have the capability to catalyze these two reactions are suitable catalysts for use in the present invention. The preferred dual-function catalyst contains a molecular sieve as the active ingredient and more specifically the molecular sieve has relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane, and most preferably, by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Å. The average effective diameter of the pores of preferred catalysts is determined by measurements described in D. W. Breck, ZEOLITE MOLECULAR SIEVES by John Wiley & Sons, New York (1974), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable dual-function catalysts may be chosen from among zeolitic molecular sieves and non-zeolitic molecular sieves.

Zeolitic molecular sieves in the calcined form may be represented by the general formula:

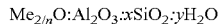

$$Me_{2/n}O:Al_2O_3:xSiO_2:yH_2O$$

where Me is a cation, x has a value from about 2 to infinity, n is the cation valence and y has a value of about 2 to 100 or more and more typically about 2 to 25.

Zeolites which may be used include chabazite—also referred to as Zeolite D, clinoptilolite, erionite, ferrierite, mordenite, Zeolite A, Zeolite P, ZSM-5, ZSM-11, and MCM-22. Zeolites having a high silica content. (i.e., Those having silica to alumina ratios greater than 10 and typically greater than 100 with best results achieved at a silica to alumina mole ratio of about 250:1 to 1000:1 are especially preferred.) One such high silica zeolite having the structure of ZSM-5 is silicalite, as the term used herein includes both the silicapolymorph disclosed in U.S. Pat. No. 4,061,724 and also the F-silicate disclosed in U.S. Pat. No. 4,073,865, hereby incorporated by reference. One of the preferred zeolites for use in the present invention has the structure of ZSM-5 and is either ZSM-5 or silicalite or a mixture thereof.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of aluminum and is at least 0.01, z is the mole fraction of phosphorous and is at least 0.01 and x+y+z=1. When EL is a mixture of metals, x represents the total amount of the element mixture present. Preferred elements (EL) are silicon, magnesium and cobalt with silicon being especially preferred.

The preparation of various ELAPOs are well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZNAPO, COAPO); U.S. Pat. No. 4,793,984 (CAPO); U.S. Pat. No. 4,752,651 and U.S. Pat. No. 4,310,440; all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

A preferred embodiment of the invention is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. No. 4,440,871; U.S. Pat. No. 5,126,308, and U.S. Pat. No. 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 Å. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 Å and less than about 5.0 Å.

The preferred OTP conversion catalyst is preferably incorporated into porous solid particles in which the catalyst is present in an amount effective to promote the desired OTP reactions. In one aspect, the porous solid particles comprise a catalytically effective amount of the molecular sieve catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are porous in nature and may or may not be effective to promote the desired OTP conversion. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieve catalyst preferably comprise about 1% to 99%, more preferably about 5% to about 90% and still more preferably about 5% to about 50%, by weight of the total composition. The preparation of solid particles comprising molecular sieve catalyst and matrix materials is conventional and well known in the art. In order to facilitate movement of the dual-function catalyst through the moving bed reactors associated with the present invention it is highly preferred that the particles of the catalyst be spherical or near spherical in shape. The diameter of these catalyst particles is preferably selected from the range of about 0.5 to 7 mm (0.02 to 0.28 in) with best results usually obtained with spherical particles that have a effective diameter of about 1.6 mm (0.063 in).

The most preferred zeolitic dual-function catalyst for use in the present invention is a zeolite having the structural configuration of ZSM-5, sometimes in the literature referred to as having a "pentasil-type" structure. A good example of this type of dual-function catalyst is disclosed in U.S. Pat. No. 7,015,369, the teachings of which are incorporated herein by reference. A borosilicate zeolite having the ZSM-5 structural configuration is disclosed as a particularly preferred dual-function catalyst in U.S. Pat. No. 4,433,188, the teachings of which are incorporated herein by reference. The dual-function use of a ZSM-5 catalyst system is disclosed in U.S. Pat. No. 4,579,999 wherein a methanol to olefin conversion zone is also charged with a recycle stream containing ethylene and a separate olefin-rich $C_5$+ gasoline stream in order to increase the yield of $C_3$ to $C_4$ olefins in the first stage MTO reaction zone disclosed therein. This '999 patent contains a good disclosure of the dual-function use of a ZSM-5 catalyst system and is specifically incorporated herein by reference. The use of a zeolitic catalyst having the mordenite structural configuration is specifically disclosed in GB 2171718 wherein a dealuminated mordenite catalyst system having a silicon to aluminum atomic ratio higher than 80:1 and a sodium oxide content less than 0.1 by weight is utilized to convert a methanol-containing feedstream and a $C_4$ olefin-rich recycle stream in order to maximize the production of propylene from these materials. All of the teachings of this '718 published patent application are specifically incorporated herein by reference.

Another particularly preferred class of dual-function catalyst for use in the present invention is the ELAPO molecular sieves. These materials are known to catalyze both the direct conversion of oxygenates to light olefins and the interconversion of olefins to a desired product olefin as can be seen from the combined teachings of U.S. Pat. No. 4,677,243 and U.S. Pat. No. 4,527,001. U.S. Pat. No. 6,455,749 has specific teachings on the use of silicoalumino phosphate catalyst (SAPO) as a dual-function catalyst and specifically has a preference for SAPO-34 as is taught in the first example contained therein. In addition the second example of this '749 patent contains a reasonably clear teaching of both the use of a SAPO-34 type of catalyst system and a ZSM-5 bound with silicalite type of catalyst system for use in the interconversion of $C_4$ olefins to other olefins. The teachings of the '243, '001 and '749 patents are hereby specifically incorporated by reference.

Best results in our invention with a non-zeolitic catalytic system are obtained when SAPO-34 is utilized as the dual-function catalyst. On the other hand best results with a zeolitic material are obtained with a ZSM-5 type of material such as the ZSM-5 materials described in the '749 patent. A particularly preferred feature of our invention is the use of a mixture of a zeolitic catalyst system with a non-zeolitic catalyst system. This mixed catalyst embodiment can be accomplished either using a physical mixture of particles containing the zeolitic material with particles containing the non-zeolitic material or the catalyst can be formulated by mixing the two types of material into a binder in order to form particles having both ingredients present therein. In either case the preferred combination is a mixture of ZSM-5 with SAPO-34 in relative amounts such that SAPO-34 comprises 30 to 70 wt-% of the molecular sieve portion of the mixture with a value of about 45 to 55 wt-% being especially preferred.

A prominent feature of the present invention is the use of moving bed technology in a OTP process in order to enhance the selectivity of the process for propylene production. The use of moving bed technology in a classical MTO process is known and is shown in U.S. Pat. No. 5,157,181, all of the teachings of which are hereby incorporated by reference. This '181 patent does not however specifically address the application of this technology to the problem of maintenance of high propylene selectivity in a process for converting oxygenate to propylene, nor does the '181 patent provide any information on the effect of catalyst circulation rate on the propylene average cycle yield, particularly in the context where light and heavy olefin recycle is used in order to maximize propylene yield by using the dual-function catalyst to promote not only the oxygenate to olefin reaction but also the olefin interconversion reactions discussed above. Moving bed reactors and regeneration systems suitable for use in accordance with the present invention are well known in the art and have been widely employed commercially for example in the reforming of naphtha fractions to increase octane number and to facilitate the dehydrogenation of light paraffins to make olefins.

Moving bed reaction zones can be configured in a number of ways, for instance, the catalyst particles can be introduced to an upper section of the reaction zone and fed by gravity through the entire volume of the reaction zone, wherein the catalyst is contacted with the feedstream either in a countercurrent direction to the catalyst movement or in a concurrent direction. In a preferred aspect of the present invention the feedstream flow is countercurrent to the catalyst flow, that is, the feedstream is introduced into a lower portion of the reaction zone and withdrawn from an upper portion thereof. This preferred configuration can provide substantial advantages in OTP conversion reactions because the feedstream is thereby contacted with partially deactivated catalyst during the initial stages of the conversion when the driving force is high, and more active catalysts during the subsequent stages of the conversion when the driving force is lower.

More typically the catalyst particles are introduced into an annulus defined by concentric catalyst retaining screens that runs through the reaction zone, wherein the catalyst particles travel down through the annulus and are withdrawn from a lower section of the OTP reaction zone. The feedstream is introduced either to the upper or lower section of the reaction zone and is passed across the annulus generally in a direction transverse to the catalyst flow. The radial bed configuration can provide low pressure drop across the reaction zone, hence good flow distribution.

During the OTP conversion zone traversal, a carbonaceous material, i.e., coke, is deposited on the catalyst as it moved downward through the reaction zone. The carbonaceous deposit material has the effect of reducing the number of active sites on the catalyst which thereby effects the extent of the conversion and the selectivity to propylene. Thus during the moving bed conversion process a portion of the coked catalyst is withdrawn from the OTP reaction zone and regenerated to remove at least a portion of the carbonaceous material.

Preferably the carbonaceous material is removed from the catalyst by oxidative regeneration wherein the catalyst which is withdrawn from the reactor is contacted with an oxygen-containing gas at sufficient temperature and oxygen concentration to allow the desired amount of the carbonaceous materials to be removed from the catalyst. Depending upon the particular catalyst and conversion it can be desirable to substantially remove the carbonaceous material, e.g., to less than 1 wt-% and more preferably less than 0.5 wt-%. In some cases it is advantageous to only partially regenerate the catalyst, e.g., to remove from about 30 to 80 wt-% of the carbonaceous material. Preferably, the regenerated catalyst will contain about 0 to 20% and more preferably from about 0 to 10% carbonaceous material. It is preferred in most instances when relatively large concentrations of carbonaceous material (i.e. coke) are present on the catalyst, that is, greater than about 1 wt-% carbonaceous material on the catalyst, to cause the carbon burn-off to occur with an oxygen-containing gas stream which contains a relatively low concentration of oxygen. Preferably the oxygen content can be regulated through the use of inert gases or the recycling of flue gas materials to maintain an initial oxygen level in the gases which contact the highly carbonaceous containing catalyst of from about 0.5 to 2 vol.-%. By using the small concentration of oxygen, it is possible to reasonably control the oxidation of carbonaceous materials upon the catalyst without allowing excessively high temperatures to occur, thereby preventing the possibility of permanently hydrothermally damaging the molecular sieve catalyst. Temperatures used during regeneration should be in the range of about 400° to 700° C. with best results obtained at about 500° to 650° C. The details concerning the conditions for regeneration are known to those skilled in the art, for example see U.S. Pat. No. 4,873,390. The regeneration zone is preferably configured as a moving bed zone similarly to the reaction zone wherein the coked catalyst is fed to an upper portion of the regeneration zone and passed by gravity feed through the regeneration zone wherein the carbonaceous material is removed and the regenerated catalyst is withdrawn from a lower section of the regeneration zone and recirculated to the OTP reaction zone.

DETAILED DESCRIPTION OF THE DRAWING

The following description of the process of the present invention is made with reference to the attached drawing. In the interest of simplifying the description of the invention in order to facilitate understanding the drawing does not contain representations of heaters, heat exchangers, coolers, valves, control means and other conventional items that are well known to those of ordinary skill in the chemical engineering art except where their presence is essential to the understanding of the present invention.

The attached drawing shows a schematic representation of a flow scheme of the present invention in which three moving bed reaction zones, reactors 1, 2 and 3, are shown in serial configuration both with respect to the oxygenate feed and to the flow of catalyst through the reactors. The reactors themselves are shown in vertical cross section wherein the catalyst is shown flowing through an annulus which is maintained with appropriate concentric catalyst retaining screens. All three reactors operate with the charge to the reactor flowing in countercurrent relationship to the descending stream of catalyst particles. The preferred mode of operation for all three reactors is to have the oxygenate feed stream flow from the outside of the catalyst annulus traverse to the movement of the catalyst particles into the center portion from which the effluent stream is recovered. The convention used in the drawing is that the flow of feed materials, intermediate materials and product materials is represented by solid lines and the flow of catalyst to and from the reaction zones is shown by dotted lines. Catalyst is shown as being transported by a transport medium which is preferably steam, nitrogen or any of the other inert diluents previously described. The preferred catalyst transport medium is steam due to its substantial presence in the OTP reaction zone. The details associated with the mechanical equipment necessary to engage and disengage the catalyst particles as they flow from reaction zone to reaction zone and to the regeneration zone, zone 4, are well known to those skilled in the art and need not be described further.

The catalyst utilized in reactors 1, 2, and 3 is selected from the dual-function catalyst previously described and is utilized in a spherical form having a effective diameter of about 0.5 to 5 mm with a diameter of 1.6 mm being especially preferred. The total amount of OTP catalyst used is preferably divided among the three reactors in equal shares.

The selection of the number of reaction zones is based on the principle previously described of holding the conversion conditions in the individual reactors at conditions which enhance the yield of propylene. As previously explained this essentially involves reactor configurations which hold the temperature differential across the individual reactors to an amount of 80° C. or less thereby avoiding a shift in the yield structure towards ethylene and simultaneously minimizing the coke formation on the catalyst which accelerates rapidly as the temperature arises in the reaction zone due to the exothermic nature of the oxygenate to propylene conversion reactions.

For purposes of startup of the flow scheme shown in the drawing recycle lines 14, 17, 21 and 22 will be blocked off until sufficient product material is obtained for initiation of recycle. Similarly water diluent recycle through lines 13, 28 and 29 will be blocked off and instead an outside source of either water or steam will be injected into line 13 by means not shown just prior to the interconnection with line 8. At startup therefore an oxygenate feedstream will flow via line 8 to the intersection with line 13 where an appropriate amount of diluent in the form of water or steam will be admixed in order to provide an oxygenate to diluent ratio of about 0.1:1 to about 5:1 with a value of about 0.5:1 to 2:1 being especially preferred for startup. The resulting mixture of oxygenate feed and diluent will then pass through appropriate feed and effluent heat exchange and heating means (not shown) in order to vaporize the resulting stream and provide a charge stream for reactor 1 that enters the reactor at a temperature of about 350° to 475° C. and a total pressure of about 136 to 343 kPa. Sufficient catalyst will be present in reactors 1, 2, and 3 to provide a Weight Hourly Space Velocity (WHSV) of about 0.5 to 5 hr$^{-1}$ during startup with the effective WHSV rising to a level of about 1 to 10 once recycle of olefinic hydrocarbon material commences. The effluent material from reactor 1 is then withdrawn via line 9 subjected to an appropriate cooling step in order to reduce its temperature to a value close to the temperature of the charge to reactor 1 via one or more cooling means not shown, and the resulting cooled effluent stream from reactor 1 is charged to reactor 2 via line 9 and therein once again contacted with an appropriate quantity of a dual-function catalyst to convert additional amounts of oxygenate material to propylene with production of an effluent stream from reactor 2 which is withdrawn via line 10. The effluent stream from reactor 2 is once again cooled by appropriate means (not shown) to a temperature close to the inlet temperature to reactor 1 and passed via line 10 into reactor 3 where it is once again subjected to a contact with an additional amount of dual-function catalyst under conditions which result in further conversion of unreacted oxygenate to propylene and various other by-products. Appropriate measures are taken in the design of the flow paths between reactors 1 and 2 and between 2 and 3 to minimize pressure drop across these reactors and to provide temperature differentials within these reactors which are approximately the same as that experienced in reactor 1 thereby minimizing coking of the catalyst in reactors 2 and 3 to the same degree as in reactor 1.

The effluent stream from reactor 3 is then withdrawn via line 11 and subjected to an appropriate cooling step designed to liquefy a substantial amount of the water contained therein via one or more cooling means such as a feed/effluent exchanger (not shown) and passed to a three-phase separator, zone 5, in which a hydrocarbon vapor phase is formed along with a liquid hydrocarbon phase and a water phase containing significant amounts of any unreacted oxygenate that escapes from reactor 3. Since a feature of the present invention is that the activity of the dual-function catalyst is maintained at essentially start-of-cycle conditions it is expected that the amount of unreacted oxygenate that is passed into zone 5 will be minimal. In other words the overall conversion achieved during the passage of the oxygenate feed through reactors 1, 2 and 3 is expected to be 97% or greater during the entire cycle.

The aqueous phase from separator 5 is withdrawn therefrom via line 13, a drag stream therefrom is taken via line 23 in order to dispose of surplus water and the resulting net water stream is recycled via line 13 into admixture with the oxygenate feed at the junction of lines 13 and 8. Additional quantities of water can be added to reactors 2 and 3 for cooling purposes via lines 13 and 28 in the case of reactor 2 and lines 13 and 29 in the case of reactor 3. Once water recycle is initiated the startup provisions for injection of diluent water are terminated.

Returning to separator 5 the vapor phase formed therein is withdrawn via line 12 and constitutes the charge to fractionation column 6 which acts as a deethanizer and is operated to produce an ethylene-rich overhead fraction which also contains minor amounts of ethane and some methane and a bottom fraction which essentially comprises the $C_3^+$ portion of the material charged to column 6. A drag stream is withdrawn from the overhead stream produced in column 6 via line 18 in order to control the buildup of $C_1$ and $C_2$ paraffins in the ethylene recycle loop. This drag stream may be insufficient to control methane buildup in this ethylene recycle loop and under those circumstances an additional optional treatment of this ethylene rich overhead stream is necessary in order to remove methane from this stream to the point where the methane recovery is sufficient to prevent buildup of a significant methane concentration in this ethylene recycle loop. Any suitable means for demethanizing this stream may be used in this optional step which is not portrayed in the attached drawing including the use of a demethanizer column, a methane adsorption zone, a methane-selective membrane zone, and the like methane separating means. The amount of the drag stream taken by line 18 will be about 1 to 15 vol-% of the overhead stream flowing through line 14 and more typically will comprise about 1 to 10 vol-% of this stream. The remainder of the overhead stream is then charged to reactor 1 as an ethylene-rich recycle stream in accordance with the attached drawing via lines 14 and 8. It is within the scope of the present invention to apportion the ethylene-rich recycle stream flowing in line 14 between the three reactor zones but we find superior results as measured by ethylene conversion when the entire amount of this ethylene stream is charged to reactor 1 and thereby exposed to the maximum amount of available catalyst as it flows through the three reactor zones.

The bottom stream from column 6 comprising the $C_3^+$ material charged to column 6 then flows via line 15 to depropanizer column 7 wherein this $C_3^+$ stream is subjected to fractionation conditions designed to produce a propylene-rich overhead stream which is the principal product stream of the present invention and which contains minor amounts of by-product propane materials. The bottom stream from column 7 is a first stream of $C_4^+$ olefin-rich material which primarily comprises $C_4$ and $C_6$ olefinic material along with very minor amounts of butane and pentane is passed via line 17 to the intersection with line 19 where a drag stream is taken in an amount of about 1 to 15 vol-% and preferably about 1 to 3 vol-% in order to control buildup of these paraffinic materials in this $C_4^+$ olefin recycle loop. The remainder of the $C_4^+$ material flowing through line 17 is then passed into interconnections with lines 21 and 22 wherein portions are withdrawn in order to provide $C_4^+$ olefin reactants to reactors 2 and 3 via lines 21 and 22. It is to be noted that these lines are unblocked once recycle operations commence in order to facilitate the return of these $C_4^+$ olefin recycle streams. In contrast to the provision for recycle of the ethylene-rich stream which flows through line 14 into reactor 1 the preferred provision with respect to the recycle of the $C_4$ and $C_5$ olefin rich stream flowing through line 17 is to divide this stream into 3 portions and charge these portions in parallel to the three reactors. We prefer that the major portion be passed to reactor 1 and minor portions be passed to reactors 2 and 3 and in fact we prefer that 60 to 80 vol-% of the total amount of this $C_4^+$ olefin-rich recycle stream flow to reactor 1 via lines 17 and 8 with equal portions of about 10 to 20 vol-% being simultaneously charged to reactors 2 and 3 via lines 17, 23 and 9 for reactor 2 and via lines 17, 21, 22 and 10 for reactor 3.

Once the three recycle streams flowing through lines 13, 14 and 17 are up and running then the startup mode of the instant invention is terminated and the full recycle mode of operation commences with the dual-function catalyst located in reactors 1, 2 and 3 functioning not only as oxygenate conversion catalysts but also as olefin interconversion catalysts. The sequence of events in the full recycle mode is such that a oxygenate rich feedstream enters the flow scheme via line 8 is admixed with a first recycle stream which is rich in ethylene via line 14 and then passed into the intersection with line 13 where a water diluent is added in the prescribed amounts and the resulting admixture is then passed to the intersection of line 8 with line 17 where an additional quantity of $C_4^+$ olefinic material is added to form the charge to reactor 1. This charge mixture flows into reactor 1 in a manner previously described after suitable heating to the appropriate inlet temperature which is described above.

After passage through reactor 1 and thereby traversing the bed of catalyst maintained in reactor 1 in the annular space defined by the concentric retaining screens previously described the resulting effluent is withdrawn from reactor 1 via line 9 and flows to the intersection with lines 28 and 21 wherein an additional quantity of relatively cool water diluent is admixed therewith along with an additional quantity of the relatively cool $C_4^+$ olefin-rich recycle stream which is passed via line 21. After suitable additional cooling to achieve the inlet temperature set forth above the resulting mixture is then charged to reactor 2 wherein it makes a passage through a second annular bed of dual-function catalyst to produce an effluent stream that is withdrawn therefrom via line 10 and as is shown in the attached drawing admixed with an additional quantum of relatively cool water diluent which flows thereto via line 29 and an additional quantum of relatively cool $C_4^+$ olefin-rich material which flows thereto via line 22 and the resulting mixture is cooled by means not shown in the attached drawing to the hereinabove specified inlet temperature for reactor 3 and then flows through reactor 3 to encounter an additional quantity of dual-function catalyst with resulting production of effluent stream 11 which after appropriate quench and cooling flows through line 11 to three-phase separating zone 5 as previously described.

The amount of dual-function catalyst utilized in zones 1, 2 and 3 are subjected to some choice. Although a case can be made that the larger amounts of catalyst should be present in reactors 2 and 3 in order to make up for the slight amount of deactivation that will occur in reactor 1 when the catalyst flows to reactor 2 via line 25 and in reactor 3 when the catalyst flows from reactor 2 to reactor 3 via line 26, we believe that the best mode here is to run with essentially equal amounts of catalyst in the three zones or with a division which is approximately 25 to 30% of the total amount in reactors 1 and 2 with 40 to 50 vol-% of the catalyst being present in reactor 3.

Reactors 1, 2 and 3 are initially charged with the dual-function catalyst via lines not shown in the attached drawing that connect with lines 24, 25 and 26. When the OTP process is started up catalyst circulation is commenced after the reactors are lined out at operating conditions. Catalyst circulates between the reactors via lines 25 and 26 and to regenerator zone 4 via line 27. In regeneration zone 4 coke deposits are removed from the coke-containing catalyst charged thereto via line 27 using a low severity oxidative procedure as previously explained. Also charged to regeneration zone 4 by means not shown in an oxygen-containing gas stream containing about 0.5 to 2 vol-% oxygen which is supplied in an amount sufficient to support combustion of a major portion of the coke charged to this zone via 27. Regenerated catalyst is recirculated to reactor 1 via line 24, thus completing a catalyst circulation circuit defined by lines 25, 26, 27 and 24. A flue gas stream is withdrawn from zone 4 via a line not shown in the attached drawing.

A feature of the present invention is that the flow of catalyst around this catalyst circulation circuit is selected to provide a catalyst on-stream cycle time of 200 hours or less in order to maintain catalyst activity, oxygenate conversion and propylene selectivity at or near start of cycle conditions. In other words, the flow rate of catalyst particles around this circuit is set such that a catalyst particle's residence time in reactors 1, 2 and 3 is not more than 200 hours before it is returned to zone 4 for regeneration.

Returning to three-phase separator zone 5 there is shown in the attached drawing the hydrocarbon phase formed in this zone as being withdrawn via line 30. This material generally boils in the gasoline range and can comprise a gasoline product stream of the present invention which may require further treatment due to the high content of olefinic material that is present therein. A preferred option that is not shown in the attached drawing is to subject the liquid hydrocarbon phase which is withdrawn from separator 5 via line 30 to an additional fractionation step in order to recover a $C_4^+$ olefinic rich overhead stream which can be recycled back to reactors 1, 2 and 3 in order to provide additional conversion of heavy olefins to propylene. The preferred means for recycling any such second $C_4^+$ olefin rich stream is in accordance with the disposition of the bottom stream from column 7 and in fact this second $C_4^+$ olefinic-rich stream can be directly charged to column 6 or admixed with stream flowing line 17 via means not shown prior to the junction of line 17 with line 19 wherein a drag stream would be taken in order to control paraffinic hydrocarbon buildup.

The invention claimed is:

1. A continuous process for selective conversion of an oxygenate feed to propylene wherein said oxygenate feed is consisting of at least 75% by weight DME, said continuous process comprising the steps of:
   a) reacting the oxygenate feed and a diluent in an amount corresponding to about 0.1 to 5:1 moles of diluent per mole of oxygenate with dual-function catalyst particles containing a molecular sieve, having the ability to convert at least a portion of the oxygenate to $C_3$ olefin and to interconvert $C_2$ and $C_4^+$ olefins to $C_3$ olefin, in a reaction zone containing at least three moving bed reactors wherein the reaction zone is operated at oxygenate conversion conditions selected to convert oxygenate to propylene and at a catalyst circulation rate through the reaction zone selected to result in a catalyst on-stream cycle time of 200 hours or less to produce an effluent stream containing major amounts of a $C_3$ olefin product and a water by-product and lesser amounts of a $C_2$ olefin, $C_4^+$ olefins, $C_1$ to $C_4^+$ saturated hydrocarbons and minor amounts of unreacted oxygenate, by-product oxygenates and aromatic hydrocarbons and wherein the moving bed reactors are connected in a serial flow configuration with respect to the oxygenate feed and with respect to the stream of catalyst that passes therethrough;
   b) passing the effluent stream to a separation zone and therein cooling and separating the effluent stream into a vaporous fraction rich in $C_3$ olefin, a water fraction containing unreacted oxygenate and by-product oxygenates and a liquid hydrocarbon fraction containing heavier olefins, heavier saturated hydrocarbons and minor amounts of aromatic hydrocarbons;
   c) recycling at least a portion of the water fraction recovered in step b) to step a) to provide at least a portion of the diluent used therein;
   d) separating the vaporous fraction into a $C_2$ olefin-rich fraction, a $C_3$ olefin-rich product fraction and a first $C_4^+$ olefin-rich fraction;
   e) recycling at least a portion of the $C_2$ olefin-rich fraction or of the first $C_4^+$ olefin-rich fraction or of a mixture of these fractions to step a); and
   f) withdrawing coke-containing dual-function catalyst particles from the reaction zone, oxidatively regenerating the withdrawn catalyst particles in a regeneration zone and returning a stream of regenerated catalyst particles to the reaction zone.

2. The continuous process as defined in claim 1 wherein the dual function catalyst contains a zeolitic molecular sieve.

3. The continuous process as defined in claim 2 wherein the zeolitic molecular sieve has a structure corresponding to ZSM-5.

4. The continuous process as defined in claim 1 wherein the dual-function catalyst contains an ELAPO molecular sieve.

5. The continuous process as defined in claim 4 wherein the ELAPO molecular sieve is a SAPO material having a structure corresponding to SAPO-34.

6. The continuous process as defined in claim 1 wherein the dual-function catalyst contains a mixture of a zeolitic molecular sieve and an ELAPO molecular sieve.

7. The continuous process as defined in claim 1 when the liquid hydrocarbon fraction separated in step b) is further separated into a second $C_4^+$ olefin-rich fraction and a naphtha product fraction.

8. The continuous process as defined in claim 7 wherein at least a portion of the second $C_4^+$ olefin-rich fraction is recycled to step a).

9. The continuous process as defined in claim 7 wherein at least a portion of the $C_2$ olefin-rich fraction, the first $C_4^+$ olefin-rich fraction and the second $C_4^+$ olefin-rich fraction are recycled to step a).

10. The continuous process as defined in claim 1 wherein the diluent used in step a) is steam, methane, an aromatic hydrocarbon or a mixture thereof.

11. The continuous process as defined in claim 1 wherein said oxygenate feed is consisting of at least 90% by weight DME.

12. The continuous process as defined in claim 1 wherein said oxygenate feed is consisting of at least 95% by weight DME.

13. The continuous process as defined in claim 1 wherein said oxygenate feed is consisting of at least 99% by weight DME.

14. The continuous process as defined in claim 1 wherein said oxygenate feed consists essentially of DME.

* * * * *